United States Patent [19]

Cragoe, Jr.

[11] 4,342,782
[45] Aug. 3, 1982

[54] 1-(SUBSTITUTED-AMINOALKOXY-PHENYL)-2-METHYLENE-1-ALKANONES, COMPOSITIONS AND USE THEREOF

[75] Inventor: Edward J. Cragoe, Jr., Lansdale, Pa.

[73] Assignee: Merck & Co., Inc., Rahway, N.J.

[21] Appl. No.: 961,422

[22] Filed: Nov. 16, 1978

[51] Int. Cl.³ .................... A61K 31/135; C07C 97/10
[52] U.S. Cl. ............................... 424/330; 424/248.58;
 424/263; 424/267; 424/274; 544/174; 546/340;
 260/326.5 J; 260/501.21; 564/353; 564/354;
 424/316
[58] Field of Search ...................... 260/570.7, 501.21;
 544/174; 424/330, 248.58, 316

[56] References Cited

U.S. PATENT DOCUMENTS

| | | | |
|---|---|---|---|
| 2,668,813 | 2/1954 | Goldberg et al. | 260/570.7 |
| 2,668,850 | 2/1954 | Goldberg et al. | 260/570.7 |
| 3,255,241 | 6/1966 | Schultz et al. | 260/516 |
| 3,322,832 | 5/1967 | Cragoe, Jr. | 260/592 |
| 3,409,661 | 11/1968 | Schultz et al. | 260/471 |
| 3,458,563 | 7/1969 | Cragoe, Jr. | 260/316 |
| 3,514,482 | 5/1970 | Cragoe, Jr. | 260/521 |
| 3,538,154 | 11/1970 | Cragoe, Jr. et al. | 260/521 |
| 3,855,296 | 12/1974 | Griot | 260/570.7 |
| 3,919,327 | 11/1975 | Lednicer | 260/570.7 |

FOREIGN PATENT DOCUMENTS 1447252  6/1966  France .............................. 260/570.7

OTHER PUBLICATIONS

Fisons Corporation Technical Bulletin, "Intal", No. (02–0670–60–3), Jul. 1974.
Fed. Proc. 36 (3), 5014 (1977).

*Primary Examiner*—Robert W. Ramsuer
*Attorney, Agent, or Firm*—Raymond M. Speer; Michael C. Sudol, Jr.

[57] ABSTRACT

1-(Substituted-aminoalkoxyphenyl)-2-methylene-1-alkanones, a class of compounds possessing antiallergic properties for use in the treatment of allergic conditions, such as asthma prepared by etherifying an alkanoylphenol with an aminoalkyl halide, converting the ether formed to a salt of Mannich base by reacting it with a salt of a secondary amine in the presence of formaldehyde or paraformaldehyde and treating the Mannich salt with a weak base to deaminate the same and form the final product.

14 Claims, No Drawings

1-(SUBSTITUTED-AMINOALKOXYPHENYL)-2-METHYLENE-1-ALKANONES, COMPOSITIONS AND USE THEREOF

BACKGROUND OF THE INVENTION

This invention relates to 1-substituted-aminoalkoxyphenyl-1-alkanones and a method of preparing the same, of the following general formula:

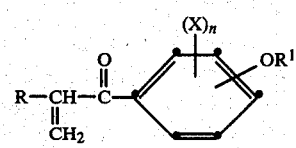

wherein R is a straight or branched chain lower alkyl radical of from 1-5 carbon atoms, such as methyl, ethyl, propyl, isopropyl, butyl, etc. or trihalomethyl substituted lower alkyl ($C_{1-5}$) radical such as 2,2,2-trifluoroethyl, 2,2,2-trifluoroisopropyl, or a cycloalkyl radical of 3 to 6 carbon atoms, such as cyclobutyl, cyclopentyl, cyclohexyl, etc. or the radicals

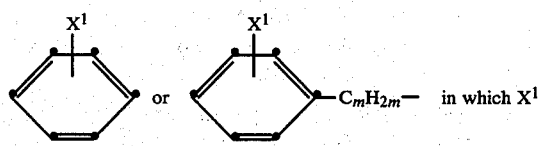

is hydrogen, halogen or lower alkyl having from 1-5 carbon atoms and m is an integer from 1 to 5; X represents similar or dissimilar members selected from the group consisting of hydrogen, straight or branched chain lower alkyl having from 1-5 carbon atoms or halogen such as chlorine, bromine, iodine or fluorine, or when taken together two X radicals on adjacent carbon atoms of the benzene ring to which they are attached they may be joined to form the 1,3-butadienylene linkage, i.e. —CH=CH—CH=CH—; n is an integer from 1 to 4; and $R^1$ is alkylaminoalkyl, such as dimethylaminoethyl, diethylaminoethyl, diethylaminopropyl, dimethylaminoisobutyl, etc. N-alkyl substituted five-membered saturated heterocycles containing one N atom, such as pyrrolidino-N-ethyl, N-alkyl substituted six-membered saturated heterocycles containing one N atom, such as piperidinoethyl or N-alkyl substituted six-membered saturated heterocycles containing one O and one N atoms, such as morpholinoethyl, a nitrogen containing heterocyclic-alkyl group, such as pyridylmethyl, pyridylethyl and the like and their pharmaceutically acceptable acid addition salts, such as their hydrochlorides, isethionates, sulfates, acetates, propionates, maleates, succinates, benzenesulfonates, p-toluenesulfonates, and the like.

The products of this invention are antiallergic agents which can be used in the treatment of conditions associated with allergies, such as asthma, asthmatic form bronchitis of allergic origin. When administered in therapeutic dosages, in conventional vehicles, the instant products effectively alleviate conditions usually associated with allergies, particularly those associated with histamine.

The preferred embodiment of the invention, i.e., those compounds which possess the greatest antiallergic activity, are those which have the following general formula:

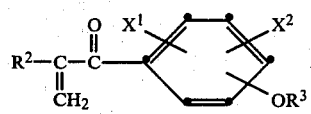

wherein $R^2$ is straight or branched chain lower alkyl, $X^2$ is hydrogen, halogen or methyl, $X^3$ is halogen or methyl and $R^3$ is lower alkylamino lower alkyl, morpholino lower alkyl or pyridylmethyl.

One of the methods of preparing the instant compounds involves a two step process. In the first, the 4-alkanoylphenols are etherified with a substituted aminoalkyl halide or pyridylmethyl halide such as the chloride, bromide, or iodide, viz:

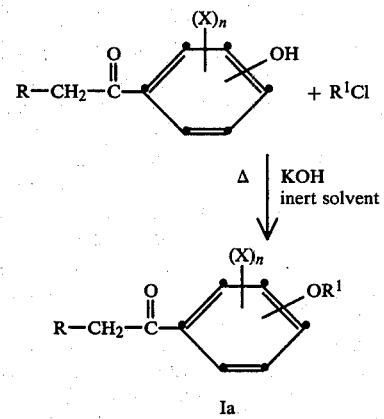

In the second stage the ethers Ia thus formed are converted to the salts of a Mannich base Ib by reacting them with a salt of a secondary amine in the presence of formaldehyde or paraformaldehyde and then treating the Mannich salt with a weak base to deaminate the same and form the final product, II, viz:

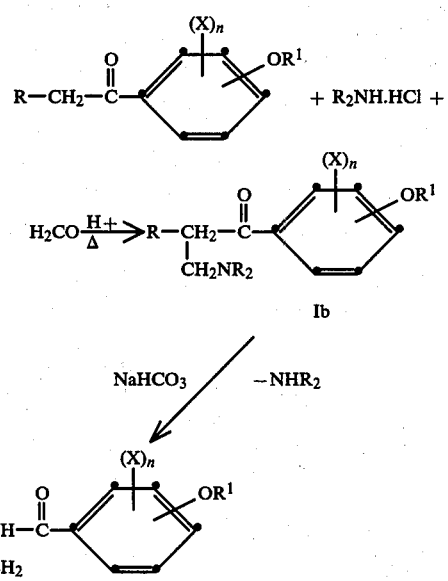

The first stage or etherification is generally carried out by adding a solution of the substituted aminoalkyl halide, preferably the chloride in a solvent such as isopropanol to an equimolar solution of the 4-alkanoylphenol in the same solvent containing an alkali hydroxide such as KOH, NaOH, etc. and heating to complete the reaction. Then the reaction mixture is cooled, filtered and concentrated to dryness. The residue is extracted with a solvent such as ether and the solvent evaporated or distilled to recover the residual etherified product Ia.

These 1-(substituted aminoalkoxyphenyl)-1-alkanones having the general formual:

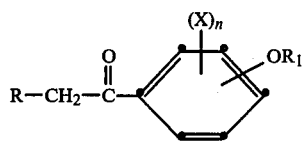

wherein R, R$^1$, X and n are as defined hereinbefore, are in themselves new products useful as intermediates in the preparation of the final products II, namely 1-(substituted-aminoalkoxyphenyl)-2-methylene-1-alkanones.

In the second stage, the aforementioned intermediates Ia are converted to the salts of a Mannich base as indicated above, using dimethyl amine as the preferred secondary amine. Weak bases other than sodium bicarbonate can of course also be used to effect dehydroamination of the Mannich salts. Generally a mixture of the ether Ia, the dimethylamine hydrochloride and the formaldehyde or paraformaldehyde in a molar ratio of 1:1:2 plus conc. HCl are heated on a steam bath for a few hours. The mixture is digested with water and filtered and to the filtrate containing the Mannich salt is added an aqueous solution of sodium bicarbonate and again heated on a steam bath, after which the reaction product is extracted with a solvent, such as ether, washed, dried and distilled in vacuo to obtain the final product II, namely 1-(substituted-aminoalkoxyphenyl)-2-methylene-1-alkanones.

A second synthetic method involves the reaction of a (2-methylenealkanoyl)phenol III with a substituted-aminoalkyl halide, such as chloride, bromide or iodide, in the presence of a base. Thus,

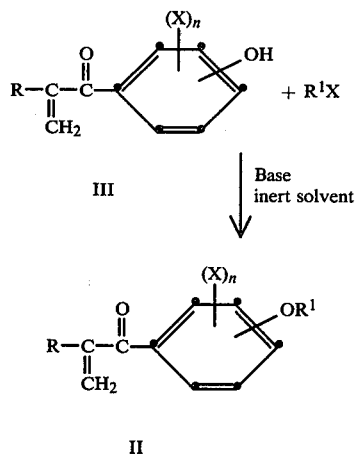

This reaction is carried out by adding to a solution of the (2-methylenealkanoyl)phenol III in an inert solvent such as dimethylformamide, N-methylpyrrolidinone and the like, a base such as potassium carbonate, sodium carbonate and the like. The reaction mixture is then treated with a substituted aminoalkyl halide and the mixture heated at 30°–70° for 1 to 6 hours. The product is isolated by adding water to the reaction mixture, extracting the product with ether, drying over an anhydrous sodium sulfate and distilling at reduced pressure.

The free bases prepared by either method can be converted to the desired acid addition salts by dissolving the base in a solvent such as ether, benzene, carbon tetrachloride and the like and adding an equivalent weight of the appropriate acid, such as hydrochloric acid, isethionic acid, sulfuric acid, acetic acid, propionic acid, maleic acid, malic acid, succinic acid, benzene sulfonic acid, p-toluenesulfonic acid, filtering the acid addition salt and drying.

Illustrative, but non-limitative, examples of the preparation of the instant compounds are as follows:

EXAMPLE 1

1-[2-Chloro-4-(2-diethylaminoethoxy)phenyl]-2-methylene-1-butanone

Step A:

1-[2-Chloro-4-(2-diethylaminoethoxy)phenyl]-1-butanone

A solution of 3.5 g. (0.02 mole) of 2-diethylaminoethyl chloride hydrochloride in 40 ml. of isopropanol and 5 ml. of water is added to a solution of 3.98 g. (0.02 mole) of 3-chloro-4-butyrylphenol in 85 ml. of isopropanol containing 2.6 g. (0.045 mole) of potassium hydroxide. The mixture is heated on the steam bath for 4 hrs., cooled, filtered and concentrated to dryness in vacuo.

The residue is heated with water and extracted with ether. The ether extract is washed with water, dilute (2%) sodium hydroxide, water, dried over sodium sulfate, filtered and evaporated to dryness on the steam bath. The product is obtained upon distillation in vacuo (0.3 mm.) as a pale yellow oil.

Analysis for $C_{16}H_{24}ClNO_2$: Calc.: C, 64.53; H, 8.12; N, 4.70; Found: C, 64.80; H, 8.19; N, 4.55.

Step B:

1-[2-Chloro-4-(2-diethylaminoethoxy)phenyl]-2-methylene-1-butanone

A mixture of 8.9 g. (0.03 mole) of 1-[2-chloro-4-(2-diethylaminoethoxy)phenyl]-1-butanone, 2.7 g. (0.033 mole) of dimethylamine hydrochloride, 1.8 g. (0.06 mole) of paraformaldehyde and 5 ml. of concentrated hydrochloric acid is heated on the steam bath for 2 hours. The mixture is digested on the steam bath with 700 ml. of water, filtered and the filtrate added to 350 ml. of 10% aqueous sodium bicarbonate. The solution is heated on the steam bath for 1 hr., cooled and extracted with ether. The ether extract is washed with water, dried over sodium sulfate, filtered and evaporated to dryness on the steam bath. The product is obtained upon distillation in vacuo (0.3 mm.) as a pale yellow oil.

Analysis for $C_{17}H_{24}ClNO_2$: Calc.: C, 65.90; H, 7.81; N, 4.52; Found: C, 65.75; H, 7.60; N, 4.59.

EXAMPLE 2

1-[2-Chloro-4-(2-dimethylaminoethoxy)phenyl]-2-methylene-1-butanone

Step A:
1-[2-Chloro-4-(2-dimethylaminoethoxy)phenyl]-1-butanone

By substituting 2.9 g. (0.02 m.) of 2-dimethylaminoethyl chloride hydrochloride for 2-diethylaminoethyl chloride hydrochloride in Example 1 Step A and carrying out the reaction as described in Example 1 Step A, the product is obtained as a pale yellow oil upon distillation in vacuo (0.3 mm.).

Analysis for $C_{14}H_{20}ClNO_2$: Calc.: C, 62.33; H, 7.47; N, 5.19; Found: C, 62.34; H, 7.36; N, 5.03.

Step B:
1-[2-Chloro-4-(2-dimethylaminoethoxy)phenyl]-2-methylene-1-butanone By substituting 1-[2-chloro-4-(2-dimethylaminoethoxy)phenyl]-1-butanone (8.1 g., 0.03 mole) for 1-[2-chloro-4-(2-diethylaminoethoxy)phenyl]-1-butanone in Example 1 Step B and carrying out the reaction as described therein, the product is obtained as a yellow oil upon distillation in vacuo (0.3 mm.).

Analysis for $C_{15}H_{20}ClNO_2$: Calc.: C, 63.95; H, 7.15; N, 4.97; Found: C, 63.69; H, 7.25; N, 5.08.

EXAMPLE 3

1-[2-Chloro-4-(3-diethylaminopropoxy)phenyl]-2-methylene-1-butanone

Step A:
1-[2-Chloro-4-(3-diethylaminopropoxy)phenyl]-1-butanone

This compound is prepared by essentially the same procedure as described in Example 1 Step A except that the 2-diethylaminoethyl chloride hydrochloride of Example 1 Step A is replaced by an equimolecular quantity of 3-diethylaminopropyl chloride hydrochloride. The product is obtained as a colorless oil upon distillation in vacuo (0.2 mm.).

Analysis for $C_{17}H_{26}ClNO_2$: Calc.: C, 65.47; H, 8.40; N, 4.49; Found: C, 65.60; H, 8.47; N, 4.45.

Step B:
1-[2-Chloro-4-(3-diethylaminopropoxy)phenyl]-2-methylene-1-butanone This compound is prepared by essentially the same method as described in Example 1 Step B except that the 1-[2-chloro-4-(2-diethylaminoethoxy)phenyl]-1-butanone of Example 1 Step B is replaced by an equimolecular quantity of 1-[2-chloro-4-(3-diethylaminopropoxy)phenyl]-1-butanone. The product is obtained as a yellow oil upon distillation in vacuo (0.4 mm.).

Analysis for $C_{18}H_{26}ClNO_2$: Calc.: C, 66.76; H, 8.09; N, 4.33; Found: C, 66.31; H, 7.93; N, 4.34.

EXAMPLE 4

1-[2-Chloro-4-(3-dimethylamino-2-methylpropoxy)phenyl]-2-methylene-1-butanone

Step A:
1-[2-Chloro-4-(3-dimethylamino-2-methylpropoxy)phenyl]-1-butanone

This compound is prepared by essentially the same procedure as described in Example 1 Step A except that the 2-diethylaminoethyl chloride hydrochloride of Example 1 Step A is replaced by an equimolecular quantity of 3-dimethylamino-2-methylpropyl chloride hydrochloride. The product is obtained as a colorless oil upon distillation in vacuo (0.3 mm.).

Analysis for $C_{16}H_{24}ClNO_2$: Calc.: C, 64.53; H, 8.12; N, 4.70; Found: C, 64.63; H, 7.86; N, 4.60.

Step B:
1-[2-Chloro-4-(3-dimethylamino-2-methylpropoxy)phenyl]-2-methylene-1-butanone This compound is prepared by essentially the same procedure as described in Example 1 Step B except that the 2-chloro-4-(2-diethylaminoethoxy)butyrophenone of Example 1 Step B is replaced by an equimolecular quantity of 1-[2-chloro-4-(3-dimethylamino-2-methylpropoxy)phenyl]-1-butanone. The product is obtained as a yellow oil upon distillation in vacuo (0.3 mm.).

Analysis for $C_{17}H_{24}ClNO_2$: Calc.: C, 65.90; H, 7.81; N, 4.52; Found: C, 65.92; H, 7.73; N, 4.33.

EXAMPLE 5

1-2-Chloro-4-[2-(N-pyrrolidinyl)ethoxy]phenyl-2-methylene-1-butanone

Step A:
1-{2-Chloro-4-[2-(N-pyrrolidinyl)ethoxy]-phenyl}-1-butanone

This compound is prepared by essentially the same procedure as described in Example 1 Step A except that the 2-diethylaminoethyl chloride hydrochloride of Example 1 Step A is replaced by an equimolecular quantity of N-(2-chloroethyl)pyrrolidine hydrochloride. The product is obtained as a pale yellow oil upon distillation in vacuo (0.3 mm.).

Analysis for $C_{16}H_{22}ClNO_2$: Calc: C, 64.96; H, 7.50; N, 4.74; Found: C, 64.97; H, 7.33; N, 4.68.

Step B:
1-{2-Chloro-4-[2-(N-pyrrolidinyl)ethoxy]-phenyl}-2-methylene-1-butanone This compound is prepared by essentially the same procedure as described in Example 1 Step B except that the 1-{2-chloro-4-(2-diethylaminoethoxy)phenyl}-1-butanone of Example 1 Step B is replaced by an equimolecular quantity of 1-{2-chloro-4-[2-N-pyrrolidinyl)ethoxy]phenyl}-1-butanone. The product is obtained as a yellow oil upon distillation in vacuo (0.3 mm.).

Analysis for $C_{17}H_{22}ClNO_2$: Calc.: C, 66.33; H, 7.20; N, 4.55; Found: C, 65.98; H, 7.16; N, 4.54.

EXAMPLE 6

1-[2-Chloro-4-(2-piperidinoethoxy)phenyl]-2-methylene-1-butanone

Step A:
1-[2-Chloro-4-(2-piperidinoethoxy)phenyl]-1-butanone

This compound is prepared by essentially the same procedure as described in Example 1 Step A except that the 2-diethylaminoethyl chloride hydrochloride of Example 1 Step A is replaced by an equimolecular quantity of N-(2-chloroethyl)piperidine hydrochloride. The product is obtained as a pale yellow oil upon distillation in vacuo (0.3 mm.).

Analysis for $C_{17}H_{24}ClNO_2$: Calc.: C, 65.90; H, 7.81; N, 4.52; Found: C, 66.15; H, 8.00; N, 4.44.

Step B:
1-[2-Chloro-4-(2-piperidinoethoxy)phenyl]-2-methylene-1-butanone

This compound is prepared by essentially the same procedure as described in Example 1 Step B except that the 1-[2-chloro-4-(2-diethylaminoethoxy)phenyl]-1-butanone of Example 1 Step B is replaced by an equimolecular quantity of 1-[2-chloro-4-(2-piperidinoethoxy)phenyl]-1-butanone. The product is obtained as a yellow oil upon distillation in vacuo (0.3 mm.).

Analysis for $C_{18}H_{24}ClNO_2$: Calc.: C, 67.17; H, 7.52; N, 4.35; Found: C, 67.20; H, 7.44; N, 4.30.

EXAMPLE 7
1-[2-Chloro-4-(2-morpholinoethoxy)phenyl]-2-methylene-1-butanone

Step A:
1-[2-Chloro-4-(2-morpholinoethoxy)phenyl]-1-butanone

This compound is prepared by essentially the same procedure as described in Example 1 Step A except that the 2-diethylaminoethyl chloride hydrochloride of Example 1, Step A is replaced by an equimolecular quantity of N-(2-chloroethyl)morpholine hydrochloride. The product is obtained as a colorless oil upon distillation in vacuo (0.3 mm.).

Analysis for $C_{16}H_{22}ClNO_3$: Calc.: C, 61.63; H, 7.11; N, 4.49; Found: C, 61.49; H, 7.11; N, 4.41.

Step B:
1-[2-Chloro-4-(2-morpholinoethoxy)phenyl]-2-methylene-1-butanone This compound is prepared by essentially the same procedure as described in Example 1 Step B except that the 1-[2-chloro-4-(2-diethylaminoethoxy)phenyl]-1-butanone of Example 1, Step B is replaced by an equimolecular quantity of 1-[2-chloro-4-(2-morpholinoethoxy)phenyl]-1-butanone. The product is obtained as a yellow oil upon distillation in vacuo (0.3 mm.).

Analysis for $C_{17}H_{22}ClNO_3$: Calc.: C, 63.05; H, 6.85; N, 4.33; Found: C, 63.17; H, 6.90; N, 4.33.

EXAMPLE 8
1-[2,3-Dichloro-4-(2-diethylaminoethoxy)-phenyl]-2-methylene-1-butanone To a solution of 2,3-dichloro-4-(2-methylenebutyryl)-phenol (17.40 g.; 0.071 mole) in dimethylformamide (70 ml.) is added potassium carbonate (21.70 g.; 0.157 mole). Then diethylaminoethyl chloride++ (21.37 g.; 0.157 mole) is added and the mixture is stirred at 55°–60° for 3 hours.

++(Diethylaminoethyl chloride is obtained by dissolving diethylaminoethyl chloride hydrochloride (30.00 g.; 0.174 mole) in water (15 ml.) and adding excess 10N sodium hydroxide solution. The liberated free base is extracted into ether and the combined extracts are dried over anhydrous potassium carbonate. The solvent is removed under vacuum to give 21.37 g. of a colorless residual oil.)

The cooled reaction mixture is poured into water (250 ml.) and the resulting oil is extracted into ether. The combined extracts are washed with 5% sodium hydroxide solution, then water and dried over anhydrous sodium sulfate. The solvent is removed under vacuum and the residual oil is distilled to give 1-[2,3-dichloro-4-(2-diethylaminoethoxy)phenyl]-2-methylene-1-butanone as a yellow oil, yield 15.84 g. (65%), b.p. 163°–165°/0.1 mm.

EXAMPLE 9
1-[2,3-Dichloro-4-(2-diethylaminoethoxy)phenyl]-2-methylene-1-butanone p-toluenesulfonate A solution of 1-[2,3-dichloro-4-(2-diethylaminoethoxyphenyl]-2-methylene-1-butanone (15.84 g.; 0.046 mole) in ether (150 ml.) is treated with a solution of p-toluenesulfonic acid monohydrate (9.70 g.; 0.051 mole) in ether (200 ml.). The resulting white solid is collected, washed with ether and dried. The yield is 20.20 g. (85%), m.p. 103°–105°. Recrystallization from butyl chloride gives white needles, m.p. 103°–105°.

Analysis for $C_{24}H_{31}Cl_2NO_5S$: Calc.: C, 55.81; H, 6.05; N, 2.71; Found: C, 55.70; H, 6.14; N, 2.76.

In a manner similar to that described in Example 1, Steps A and B for the preparation of 1-[2-chloro-4-(2-diethylaminoethoxy)phenyl]-2-methylene-1-butanone, all of the products of the invention may be obtained. Thus, by substituting the appropriate substituted aminoalkyl halide alkanoylphenyl for the diethylaminoethyl chloride and the 3-chloro-4-butyrylphenol reactants recited in Example 1, Step A and following the procedure described therein all of the intermediate 1-(substituted-aminoalkoxyphenyl)-1-alkanone products of the invention may be obtained. Similarly by substituting the 1-[2-chloro-4-(2-diethylaminoethoxy)phenyl]-1-butanone of Example 1, Step B, with an equimolar quantity of the appropriate intermediate 1-(substituted-aminoalkoxyphenyl)-1-alkanone and following the procedure of Example 1, Step B, there is obtained all the 1-(substituted-aminoalkoxyphenyl)-2-methylene-1-alkanone compounds of the invention.

Additional examples of compounds coming within the purview of the instant invention and represented by the following general formula:

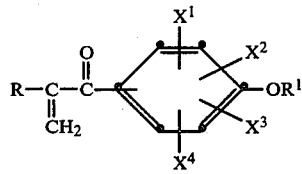

are shown in the following Table I.

TABLE I

| Example | R—C—C(=O) / ‖CH₂ | $X^1$ | $X^2$ | $X^3$ | $X^4$ | $R^1$ |
|---|---|---|---|---|---|---|
| 10 | 4-(CH₃)₂CHC—CO— / ‖CH₂ | 2-H | 3-Cl | 5-H | 6-H | 3-dimethylamino-2-methylpropyl |

TABLE I-continued

| Example | R—C(=CH₂)—C(=O)— | X¹ | X² | X³ | X⁴ | R¹ |
|---|---|---|---|---|---|---|
| 11 | 4-CF₃CH₂C(=CH₂)—CO— | 2-CH₃ | 3-Cl | 5-H | 6-H | 2-dimethylaminoethyl |
| 12 | 4-CH₃C(=CH₂)—CO— | 2-Cl | 3-H | 5-CH₃ | 6-H | morpholino-N-ethyl |
| 13 | 4-C₂H₅C(=CH₂)CO— | 2-H | 3-Cl | 5-CH₃ | 6-CH₃ | 2-diethylaminoethyl |
| 14 | 4-C₂H₅—C(=CH₂)—CO— | 2-Cl | 3-CH₃ | 5-CH₃ | 6-CH₃ | morpholino-N-ethyl |
| 15 | 4-(phenyl)C(=CH₂)—CO— | 2-Cl | 3-H | 5-H | 6-H | 2-diethylaminomethyl |
| 16 | 4-(cyclopropyl)C(=CH₂)—CO— | 2-H | 3-Cl | 5-H | 6-H | 3-dimethylamino-2-methylpropyl |
| 17 | 4-C₂H₅C(=CH₂)—CO— | 2,3-CH₂—CH₂—CH₂—CH₂— | | 5-H | 6-H | 2-dimethylaminoethyl |
| 18 | 4-CH₃(CF₃)CHC(=CH₂)—CO— | 2-Cl | 3-H | 5-H | 6-H | morpholino-N-methyl |
| 19 | 3-C₂H₅—C(=CH₂)—CO— | 2-H | 4-Cl | 5-H | 6-H | 2-dimethylaminoethyl |
| 20 | 2-C₂H₅C(=CH₂)—CO— | 3-Cl | 4-H | 5-Cl | 6-H | 2-diethylaminoethyl |

In a manner similar to that described in Example 8 for the preparation of 1-[2,3-dichloro-4-(2-diethylaminoethoxy)phenyl]-2-methyl-1-butanone, all the products of the invention may be obtained. Thus, by substituting an equimolar amount of the appropriate substituted-aminoalkyl halide and (2-methylenealkanoyl)phenol for the 2,3-dichloro-4-(2-methylenebutyryl)phenol and the diethylaminoethyl chloride reactants recited in Example 8 and following the procedure recited therein, all the products of the invention may be obtained.

Additional examples of the compounds coming within the purview of the instant invention and represented by the following general formula:

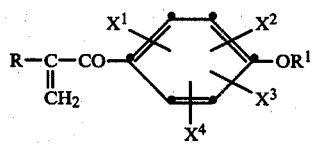

are shown in Table II.

| Example | R | X¹ | X² | X³ | X⁴ | R¹ |
|---|---|---|---|---|---|---|
| 21 | 4-C₂H₅C(=CH₂)—CO— | 2-Cl | 3-Cl | 5-H | 5-H | —CH₂(2-pyridyl) |
| 22 | 4-C₂H₅—C(=CH₂)—CO— | 2-Cl | 3-Cl | 5-H | 6-H | —CH₂(3-pyridyl) |

-continued

| Example | R | $X^1$ | $X^2$ | $X^3$ | $X^4$ | $R^1$ |
|---|---|---|---|---|---|---|
| 23 | 4-$C_2H_5$—C—CO—<br>‖<br>$CH_2$ | 2-Cl | 3-Cl | 5-H | 6-H | —$CH_2$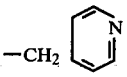 |
| 24 | 4-$C_2H_5$—C—CO<br>‖<br>$CH_2$ | 2-$CH_3$ | 3-$CH_3$ | 5-H | 6-H | —$CH_2$—$CH_2N(CH_3)_2$ |
| 25 | 4-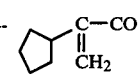—C—CO—<br>‖<br>$CH_2$ | 2,3-CH=CH—CH=CH | | 5-H | 6-H | —$CH_2CH_2N(CH_3)_2$ |
| 26 | 4-$C_2H_5$—C—CO—<br>‖<br>$CH_2$ | 2-Cl | 3-Cl | 5-H | 6-H | —$CH_2CH_2$N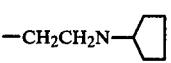 |
| 27 | 4-$C_2H_5$—C—CO—<br>‖<br>$CH_2$ | 2-Cl | 3-Cl | 5-H | 6-H | —$CH_2CH_2$N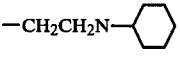 |
| 28 | 3-$C_2H_5$—C—CO—<br>‖<br>$CH_2$ | 2-H | 4-Cl | 5-Cl | 6-H | —$CH_2CH_2N(C_2H_5)_2$ |
| 29 | 2-$C_2H_5$—C—CO—<br>‖<br>$CH_2$ | 3-H | 4-Cl | 5-H | 6-Cl | —$CH_2CH_2N(CH_3)_2$ |
| 30 | 4-$CH_3$C—CO<br>‖<br>$CH_2$ | 2-Cl | 3-Cl | 5-H | 6-H | —$CH_2CH_2N(CH_3)_2$ |

The products of the invention can be administered to patients (both animal and human) in need of treatment for allergic conditions in a wide variety of therapeutic dosages in conventional vehicles as, for example, by oral administration in the form of a capsule or tablet as well as by intravenous injection. Also, the dosage of the products may be varied over a wide range as, for example, in the form of capsules or scored tablets containing 5, 10, 20, 25, 50, 100, 150, 250 and 500 milligrams, i.e., from 5 to about 500 milligrams, of the active ingredient for the symptomatic adjustment of the dosage to the patient to be treated. Generally the compounds of this invention are advantageously administered at a dosage range of from about 5 mg. to about 2,000 mg. per day or a somewhat higher or lower dosage at the physician's discretion, preferably in sub-divided amounts on a two to four times a day regimen. It will be realized by those skilled in the art that the dosage range for any particular patient (animal or human) will depend on the severity of the disease treated, weight of the patient and any other condition which the physician or other person skilled in the art will take account of. These dosages are well below the toxic or lethal dose of the products.

A suitable unit dosage form of the products can be prepared by using 100 mg. of a 1-(substituted-aminoalkoxyphenyl)-2-methylene-1-alkanones with 94 mg. of lactose and 6 mg. of magnesium stearate, and placing the 200 mg. mixture into a No. 3 gelatin capsule. Similarly, by employing more of the active ingredient and less lactose, other dosage forms can be put up in No. 3 gelatin capsules and, should it be necessary to mix more than 200 mg. of ingredients together, larger capsules may be employed. Compressed tablets, pills or other desired unit dosages can be prepared to incorporate the instant compounds by conventional methods and, if desired, can be made up as elixirs or as injectable solutions by methods well known to pharmacists.

It is also within the scope of this invention to combine two or more of the compounds of this invention in a unit dosage form or to combine one or more of the compounds with other known antiallergic agents or with other desired therapeutic and/or nutritive agents in dosage unit form.

The following example is illustrative of the preparation of the representative dosage form:

EXAMPLE 30

Dry-filled Capsules Containing 100 mg. of Active Ingredient per Capsule

| | Per Capsule |
|---|---|
| 1-[2,3-dichloro-4-(2-diethyl-aminoethoxy)phenyl]-2-methylene-1-butanone p-toluenesulfonate (Example 9) | 100 mg. |
| Lactose | 94 mg. |
| Magnesium Stearate | 6 mg. |
| Capsule Size No. 3 | 200 mg. |

The 1-[2,3-dichloro-4-(2-diethylaminoethoxy)-phenyl]-2-methylene-1-butanone p-toluenesulfonate is reduced to a No. 60 powder and then lactose and magnesium stearate are passed through a No. 60 bolting cloth onto the powder and the combined ingredients admixed for 10 minutes and then filled into No. 3 dry gelatin capsules.

Similar dry-filled capsules can be prepared by replacing the active ingredient of the above example by any of the other novel solid 1-(substituted-aminoalkoxyphenyl)-2-methylene-1-alkanone salts of this invention.

The following example is illustrative of the preparation of a representative dosage form of liquid 1-(substituted-aminoalkoxyphenyl)-2-methylene-1-alkanone compounds.

EXAMPLE 31

Oral Emulsion

| | |
|---|---|
| 1-[2,3-dichloro-4-(2-diethyl-aminoethoxy)phenyl]-2-methylene-1-butanone | 100 mg. |
| Cottonseed Oil | 600 mg. |
| Butylated Hydroxyanesole | .05 mg. |
| Arlacel 161 | 30 mg. |
| Tween 60 (polysorbate) | 30 mg. |
| Lactose | 140 g. |
| Sodium Benzoate | 0.2 gms. |
| Flavors | qs. |
| Color | qs. |
| Water | qs. ad 1000 ml. |

The 1-[2,3-dichloro-4-(2-diethylaminoethoxy)-phenyl]-2-methylene-1-butanone, cottonseed oil, butylated hydroxyanesole, Arlacel 161 and Tween 60 are mixed and heated to 65° C. The lactose and sodium benzoate are dissolved in the water and heated to 67°–70° C. This aqueous solution is added to the aforementioned mixture containing the active ingredient with agitation and cooled, the flavors and color added and the entire mixture homogenized to form the oil emulsion.

Similar unit dosage forms can be prepared by replacing the active ingredient of the above example by any of the other novel liquid compounds of this invention.

It will be apparent from the foregoing description that the 1-(substituted-aminoalkoxyphenyl)-2-methylene-1-alkanones and their intermediates constitute a valuable class of compounds which have not hitherto been prepared. One skilled in the art will also appreciate that the processes disclosed in the above examples are merely illustrative and are capable of variation and modification without departing from the spirit of the invention.

What is claimed is:

1. A compound of the general formula:

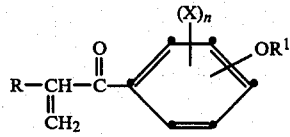

wherein R is lower alkyl, trihalomethyl substituted lower alkyl, cycloalkyl containing from 3 to 6 carbon atoms or the radicals

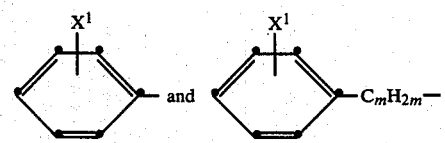

in which $X^1$ is hydrogen, halogen or lower alkyl and m is an integer from 1 to 5; X is hydrogen, lower alkyl, halogen or when taken together two X radicals on adjacent carbon atoms of the benzene ring to which they are attached may be joined to form the 1,3-butadienylene linkage; n is an integer from 1 to 4; and $R^1$ is diloweralkylaminoloweralkyl, and their pharmaceutically acceptable acid addition salts.

2. A compound of the general formula:

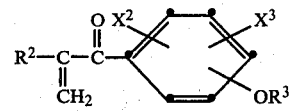

wherein $R^2$ is lower alkyl; $X^2$ is hydrogen, halogen or methyl; $X^3$ is halogen or methyl; and $R^3$ is diloweralkylamino lower alkyl.

3. The compound of claim 2 wherein $R^2$ is ethyl, $X^2$ is 2-chloro, $X^3$ is 3-chloro and $R^3O$ is 4-(2-diethylaminoethoxy); that is, 1-[2,3-dichloro-4-(2-diethylaminoethoxy)phenyl]-2-methylene-1-butanone.

4. A compound of claim 3 which is the p-toluenesulfonate salt of the compound of claim 3.

5. The compound of claim 2 wherein $R^2$ is ethyl, $X^2$ is 2-chloro, $X^3$ is hydrogen and $R^3O$ is 4-(2-dimethylaminoethoxy); that is, 1-[2-chloro-4-(2-dimethylaminoethoxy)phenyl]-2-methylene-1-butanone.

6. The compound of claim 2 wherein $R^2$ is methyl, $X^2$ is chloro, $X^3$ is 3-chloro and $R^3O$ is 4-(2-dimethylaminoethoxy), that is, 1-[2,3-dichloro-4-(2-dimethylaminoethoxy)phenyl]-2-methylene-1-propanone.

7. The compound of claim 2 wherein $R^2$ is ethyl, $X^2$ is 3-chloro, $X^3$ is 5-chloro and $R^3O$ is 4-(2-diethylaminoethoxy); that is, 1-[3,5-dichloro-2-(2-diethylaminoethoxyphenyl)-2-methylene]-1-butanone.

8. The compound of claim 7 which is the hydrochloride salt.

9. The compound of claim 2 wherein $R^2$ is ethyl, $X^2$ is 4-chloro, $X^3$ is 6-chloro and $R^3O$ is 4-(2-diethylaminoethoxy); that is, 1-[4,6-dichloro-2-(2-diethylaminoethoxy)phenyl]-2-methylene-1-butanone.

10. The compound of claim 9 which is the isethionate salt of claim 10.

11. A method of treating patients having allergic conditions which consists of administering to such patient a pharmaceutically acceptable dose of a compound of the formula:

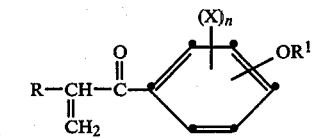

wherein R is lower alkyl, trihalomethyl substituted lower alkyl, cycloalkyl containing from 3 to 6 carbon atoms or the radicals

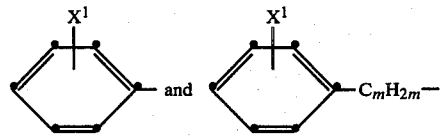

in which $X^1$ is hydrogen, halogen or lower alkyl and m is an integer from 1 to 5; X is hydrogen, lower alkyl, halogen or when taken together two X radicals on adjacent carbon atoms of the benzene ring to which they are attached may be joined to form the 1,3-butadienylene linkage; n is an integer from 1 to 4; and $R^1$ is diloweralkylaminoloweralkyl, and their pharmaceutically acceptable acid addition salts.

12. A method of treating patients having allergic conditions which consists of administering to such patient a pharmaceutically acceptable dose of a compound of the formula:

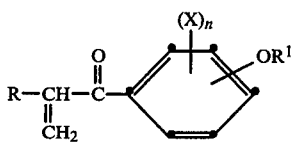

wherein $R^2$ is lower alkyl; $X^2$ is hydrogen, halogen or methyl; $X^3$ is halogen or methyl; and $R^3$ is diloweralkylamino lower alkyl.

13. A pharmaceutical composition useful in treating patients having allergic conditions which comprises as an active ingredient a compound of the formula:

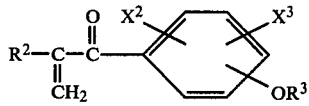

wherein R is lower alkyl, trihalomethyl substituted lower alkyl, cycloalkyl containing from 3 to 6 carbon atoms or the radicals

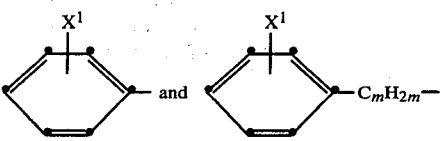

in which $X^1$ is hydrogen, halogen or lower alkyl and m is an integer from 1 to 5; X is hydrogen, lower alkyl, halogen or when taken together two X radicals on adjacent carbon atoms of the benzene ring to which they are attached may be joined to form the 1,3-butadienylene linkage; n is an integer from 1 to 4; and $R^1$ is diloweralkylaminoloweralkyl, and their pharmaceutically acceptable acid addition salts.

14. A pharmaceutical composition useful in treating patients having allergic conditions which comprises as an active ingredient a compound of the formula:

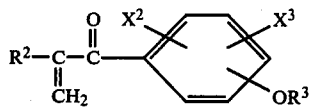

wherein $R^2$ is lower alkyl; $X^2$ is hydrogen, halogen or methyl; $X^3$ is halogen or methyl; and $R^3$ is diloweralkylamino lower alkyl.

* * * * *